(12) United States Patent
Lee

(10) Patent No.: US 9,968,296 B2
(45) Date of Patent: May 15, 2018

(54) WEARABLE SOCIO-BIOSENSOR DEVICE

(71) Applicant: CASE WESTERN RESERVE UNIVERSITY, Cleveland, OH (US)

(72) Inventor: Kiju Lee, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 223 days.

(21) Appl. No.: 15/099,963

(22) Filed: Apr. 15, 2016

(65) Prior Publication Data

US 2016/0302733 A1    Oct. 20, 2016

Related U.S. Application Data

(60) Provisional application No. 62/147,613, filed on Apr. 15, 2015.

(51) Int. Cl.

| | |
|---|---|
| *A61B 5/00* | (2006.01) |
| *A61B 5/16* | (2006.01) |
| *A61B 5/0205* | (2006.01) |
| *A61B 5/117* | (2016.01) |

(52) U.S. Cl.
CPC .......... *A61B 5/6801* (2013.01); *A61B 5/0002* (2013.01); *A61B 5/02055* (2013.01); *A61B 5/16* (2013.01)

(58) Field of Classification Search
None
See application file for complete search history.

(56) References Cited

U.S. PATENT DOCUMENTS

2014/0203797 A1 *   7/2014   Stivoric ............... A61B 5/0008
                                                        324/76.11

OTHER PUBLICATIONS

Alamaki, Heikki, Rafal Sliz, Ikram Ashraf, and Hannu Sorvoja Esko Alasaarela Matti. "Measurement of ECG, Respiratory Rate, Tilt and Temperature of a Patient and Wireless Zigbee Data Transmission."
Al-Refaie, Waddah B., et al. "Cancer trials versus the real world in the United States." Annals of surgery 254.3 (2011): 438-443.

(Continued)

*Primary Examiner* — Brian T Gedeon
(74) *Attorney, Agent, or Firm* — Tarolli, Sundheim, Covell & Tummino LLP

(57) ABSTRACT

A wearable socio-biosensor device can include a plurality of sensors to detect bio-behavioral data of a subject, social data related to a proximity of the subject to other persons wearing socio-biosensor devices and bio-behavioral data measured during the time the subject is in close proximity to other persons, and environmental data related to the subject's environment. The socio-biosensor device can also include a body portion that includes: a non-transitory memory to store the bio-behavioral data, the social data, and the environmental data; a wireless transceiver to communicate with another device based on at least one of the bio-behavioral data, the social data, and the environmental data; and a rechargeable battery. The socio-biosensor device can also include an attachment mechanism that facilitates attachment of the body portion to the subject (e.g., attached to the subject's wrist). At least one of the plurality of sensors can be embodied in the attachment mechanism.

20 Claims, 5 Drawing Sheets

(56) References Cited

OTHER PUBLICATIONS

Ashburn, Ann, et al. "Recruitment to a clinical trial from the databases of specialists in Parkinson's disease." Parkinsonism & related disorders 13.1 (2007): 35-39.
Bloom, David E., David Canning, and Günther Fink. "Implications of population ageing for economic growth." *Oxford review of economic policy* 26.4 (2010): 583-612.
De Jonge, L., et al. "Prediction of energy expenditure in a whole body indirect calorimeter at both low and high levels of physical activity." *International journal of obesity* 25.7 (2001):929.
Eea C. caMATCH: A Patient Matching Tool for Clinical Trials. In: caBIG Annual Meeting 2005.
Fearn, Paul A., et al. "A chronological database as backbone for clinical practice and research data management." *Computer-Based Medical Systems, 2003. Proceedings. 16th IEEE Symposium*. IEEE, 2003.
Heinrichs, Markus, et al. "Social support and oxytocin interact to suppress cortisol and subjective responses to psychosocial stress." *Biological psychiatry* 54.12 (2003): 1389-1398.
Hourani, Laurel L., Thomas V. Williams, and Amii M. Kress. "Stress, mental health, and job performance among active duty military personnel: findings from the 2002 Department of Defense Health-Related Behaviors Survey." *Military medicine* 171.9 (2006): 849.
Hripcsak, George. "Writing Arden Syntax medical logic modules." *Computers in biology and medicine* 24.5 (1994): 331-363.
Jacobsen, Linda A., et al. "America's aging population." *Population Bulletin* 66.1 (2011): 1-20.
Jeong, Donghwa, and Kiju Lee. "Dispersion and line formation in artificial swarm intelligence." *arXiv preprint arXiv*:1407.0014 (2014).
Jeong, Donghwa, and Kiju Lee. "Directional RSS-based localization for multi-robot applications." *Proceedings of WSEAS conf. on signal processing, robotics, and automation.* 2013.
Kim, J. M., et al. "Two algorithms for detecting respiratory rate from ECG signal." *World Congress on Medical Physics and Biomedical Engineering*2006. Springer, Berlin, Heidelberg, 2007.
Lara Jr, Primo N., et al. "Prospective evaluation of cancer clinical trial accrual patterns: identifying potential barriers to enrollment." *Journal of clinical oncology* 19.6 (2001): 1728-1733.
Lee, Kiju, Matt Moses, and Gregory S. Chirikjian. "Robotic self-replication in structured environments: Physical demonstrations and complexity measures." *The International Journal of Robotics Research* 27.3-4 (2008): 387-401.
Lee, Kiju, Georgios Kaloutsakis, and Jeremy Couch. "Towards social-therapeutic robots: How to strategically implement a robot for social group therapy?." *Computational Intelligence in Robotics and Automation (CIRA), 2009 IEEE International Symposium on*. IEEE, 2009.
Levelt, Willem. "JM (1989). Speaking. From intention to articulation." *MA: The MIT Press*, Cambridge (1981).
MarketsandMarkets website—http://www.marketsandmarkets.com/Market-Reports/wearable-sensor-market-158101489.html?gclid=CKyFxlSB8cMCFQ4vaQodoBUAzQ—accessed Sep. 6, 2016.
Moody, George B. "ECG-based indices of physical activity." *Computers in Cardiology* 1992, Proceedings of. IEEE, 1992.
Niland, J. "ASPIRE: agreement on standardized protocol inclusion requirements for eligibility." *An unpublished web resource* (2007).
Medical Advisory Secretariat. Social isolation in community-dwelling seniors: an evidence-based analysis. Ontario Health Technology Assessment Series 2008;8(5).
Pantelopoulos, Alexandros, and Nikolaos G. Bourbakis. "A survey on wearable sensor-based systems for health monitoring and prognosis." *IEEE Transactions on Systems, Man, and Cybernetics, Part C (Applications and Reviews)* 40.1 (2010): 1-12.
Perissinotto, Carla M., Irena Stijacic Cenzer, and Kenneth E. Covinsky. "Loneliness in older persons: a predictor of functional decline and death." *Archives of internal medicine* 172.14 (2012): 1078-1084.
Sahoo, Satya S., et al. "Trial prospector: matching patients with cancer research studies using an automated and scalable approach." *Cancer informatics* 13 (2014): 157.
Schenkein, Jim, ed. *Studies in the organization of conversational interaction*. Academic Press, 2014.
Smith, Judith M. "Toward a better understanding of loneliness in community-dwelling older adults." *The Journal of psychology* 146.3 (2012): 293-311.
Stone, Michelle R., Ann V. Rowlands, and Roger G. Eston. "Relationships between accelerometer-assessed physical activity and health in children: impact of the activity-intensity classification method." *Journal of sports science & medicine* 8.1 (2009): 136.
Takano, Chihiro, and Yuji Ohta. "Heart rate measurement based on a time-lapse image." *Medical engineering & physics* 29.8 (2007): 853-857.
Thoits, Peggy A. "Mechanisms linking social ties and support to physical and mental health." *Journal of health and social behavior* 52.2 (2011): 145-161.
Villa, Valentine M., et al. "The health and functional status of US veterans aged 65+: implications for VA health programs serving an elderly, diverse veteran population." *American journal of medical quality* 18.3 (2003): 108-116.
"WPI Awarded $1.9 Million to Develop Sensors that Can Save Wounded Soldiers: Three-year program funded by U.S. Army will focus on technology that could also help civilian trauma victims." *Worcester Polytechnic Institute* (Aug. 20, 2012): http://www.wpi.edu/news/20123/wounded-soldiers.html, accessed Aug. 3, 2017.
Yu, Xinguo. "Approaches and principles of fall detection for elderly and patient." *e-health Networking, Applications and Services, 2008. HealthCom 2008. 10th International Conference on*. IEEE, 2008.

\* cited by examiner

WEARABLE SOCIO-BIOSENSOR DEVICE

RELATED APPLICATION

This application claims the benefit of U.S. Provisional Application No. 62/147,613, filed Apr. 15, 2015, entitled "SYSTEM AND METHOD EMPLOYING A WEARABLE SOCIO-BIOSENSOR DEVICE". This provisional application is hereby incorporated by reference in its entirety for all purposes.

TECHNICAL FIELD

The present disclosure relates generally to a wearable socio-biosensor device and, more specifically, to systems and methods that employ the wearable socio-biosensor device.

BACKGROUND

Consumer products with wearable sensor technologies have enabled daily monitoring of biological data (e.g., heart rate, physical activity, and skin temperature) at relatively low cost. These products have shown the potential for contributing a positive impact on health outcomes for many groups of people, such as athletes, veterans, and the elderly. However, quantitative and qualitative assessment of the health impact of social interaction has mostly relied on self-reported data or external observation, which can yield limited accuracy and validity.

SUMMARY

The present disclosure relates generally to a wearable socio-biosensor device and, more specifically, to systems and methods that employ the wearable socio-biosensor device. For example, the systems and methods can employ the socio-biosensor device to provide data that can be used to assess the health impact of social interaction. This assessment of the health impact of social interaction based on directly recorded data is more accurate and valid than traditional assessments based on self-reported data or external observation. For example, the directly recorded data can include bio-behavioral data, social data, and environmental data that are measured simultaneously.

In one aspect, the present disclosure includes a wearable socio-biosensor device. The wearable socio-biosensor device can include a plurality of sensors to detect bio-behavioral data of a subject, social data related to a proximity of the subject to other persons wearing the socio-biosensors and bio-behavioral data measured during the time the subject is in close proximity to other persons, and environmental data related to the subject's environment. The socio-biosensor device can also include a body portion that includes: a non-transitory memory to store the bio-behavioral data, the social data, and the environmental data; a wireless transceiver to communicate with another device based on at least one of the bio-behavioral data, the social data, and the environmental data; a processor; and a rechargeable battery. The socio-biosensor device can also include an attachment mechanism that facilitates attachment of the body portion to the subject. At least one of the plurality of sensors can be embodied in the attachment mechanism.

In another aspect, the present disclosure also includes a method for establishing an interaction between a subject wearing a wearable socio-biosensor device and computing device. The method can include establishing a wireless communication link between the wearable socio-biosensor device worn by the subject and the computing device; downloading data from the wearable socio-biosensor device to the computing device over the wireless communication link, wherein the data comprises bio-behavioral data of the subject, social data related to a proximity of the subject to other persons wearing the socio-biosensors and bio-behavioral data measured during the time the subject is in close proximity to other persons, and environmental data related to the subject's environment; and establishing an interaction between the computing device and the subject based on the downloaded data.

In a further aspect, the present disclosure also includes a system that enables communication between a wearable socio-biosensor device and another device (e.g., a computing device, another socio-biosensor device, or the like). The system can include a wearable socio-biosensor device and another device. The wearable socio-biosensor device can include a plurality of sensors to detect bio-behavioral data of a subject, social data related to a proximity of the subject to other persons wearing the socio-biosensors and bio-behavioral data measured during the time the subject is in close proximity to other persons, and environmental data related to the subject's environment; a body portion, and an attachment mechanism that facilitates attachment of the body portion to the subject. The body portion can include a non-transitory memory to store the bio-behavioral data, the social data, and the environmental data; a wireless transceiver to communicate with another device based on at least one of the bio-behavioral data, the social data, and the environmental data; and a rechargeable battery. At least one of the plurality of sensors can be embodied in the attachment mechanism. The another device includes a wireless communication module to interface with the socio-biosensor device to receive the bio-behavioral data, the environmental data, and the social data; and a processor to recognize the subject, process the bio-behavioral data, the social data, and the environmental data, and facilitate an interaction between the another device and the subject.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
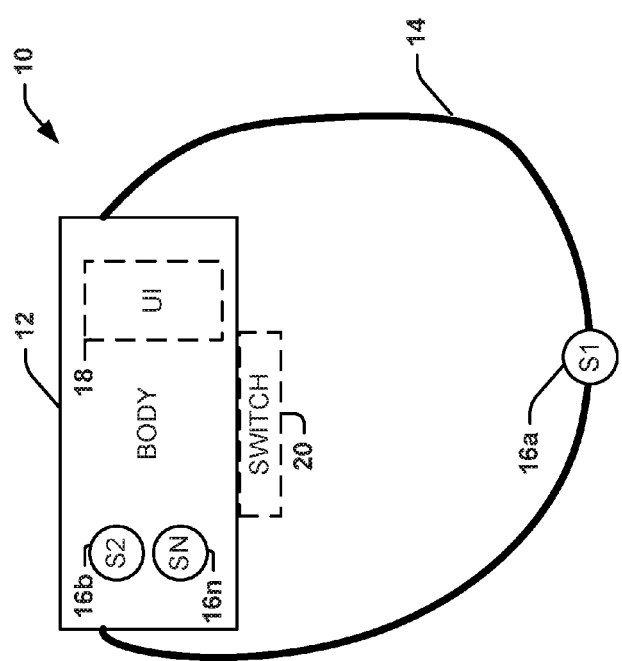
FIG. 1 is a block diagram showing an example of a wearable socio-biosensor device comprising a body and being constructed in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, when two or more devices are "coupled", a connection is established between the two or more devices. The connection can be wired, wireless, or a combination of wired and wireless. For example, respective wireless transmitters, receivers, or transceivers can be used to establish a wireless connection between the two or more devices.

As used herein, the term "module" can refer to a self-contained unit or item that can itself perform a defined task and can be linked with other such units to form a larger system. A module can include an assembly of electronic components and associated wiring and/or a segment of computer software.

As used herein, the term "computing device" can refer to a device that includes a non-transitory memory that stores instructions and a processor configured to execute the instructions to facilitate performance of one or more operations. In some instances, the non-transitory memory can also store data corresponding to the one or more operations.

As used herein, the term "real time" can refer to a system or method in which input data is processed quickly (e.g., within milliseconds) so that feedback related to the data it is available immediately or almost immediately (e.g., within milliseconds). As used herein, the term "sensor" can refer to a device that can detect or measure a physical property and records, indicates, or otherwise responds to the physical property. Examples of sensors can include, but are not limited to electrodes, infrared emitter/detectors, accelerometers, gyroscopes, thermistors, thermometers, microphones, video recorders, proximity sensors, pulse sensors, gas sensors, humidity sensors, and the like.

As used herein, the term "attachment mechanism" can generally refer to a mechanism that facilitates securing a wearable device to a user's body. For example, the attachment mechanism can include a Velcro band, a rubber strap employing magnets, a wristwatch band, or any type of mechanism that can ensure that the device remains attached to the user's body.

As used herein, the term "socio-biosensor device" can refer to a wearable device for simultaneous measurement of bio-behavioral, social, and environmental data.

As used herein, the term "social activity" can refer to an association between two or more people.

As used herein, the term "wearable" can refer to an item or device that can be worn.

As used herein, the term "user interface" can refer to a means by which a user and a computer system interact (e.g., via sound, images, graphics, and the like). In some instances, the user interface can include a graphical user interface (GUI), which can allow for visual interaction with the computer system. In other instances, the user interface can provide a visual indication, such as a light. In still other instances, the user interface can provide an audio indication.

As used herein, the term "robot device" can refer to a computing device that can interact with a socio-biosensor device. The terms "robot device" and "computing device" can be used interchangeably herein.

As used herein, the term "subject" and refer to any warm-blooded organism including, but not limited to, a human being, a pig, a rat, a mouse, a dog, a cat, a goat, a sheep, a horse, a monkey, an ape, a rabbit, a cow, etc. Unless otherwise specified, the terms "user" and "subject" can be used interchangeably herein.

II. Overview

The present disclosure relates generally to a wearable socio-biosensor device and, more specifically, to systems and methods that employ the wearable socio-biosensor device. Advantageously, the socio-biosensor devices of the present disclosure can be used for the simultaneous or real-time measurement of bio-behavioral data, social data, and/or environmental data related to a subject wearing the socio-biosensor device(s). The systems and methods of the present disclosure can employ the simultaneously recorded bio-behavioral data, social data, and/or environmental data to assess the health impact of social interaction engaged in by the subject wearing the socio-biosensor device(s). Advantageously, this assessment is more accurate and valid than traditional assessments based on self-reported data or external observation.

III. Systems

One aspect of the present disclosure can include a wearable socio-biosensor device 10 (FIG. 1). Advantageously, the wearable socio-biosensor device 10 can be used for simultaneous measurement and recording of bio-behavioral data, social data, and/or environmental data for a subject wearing the socio-biosensor device. In some examples, the bio-behavioral data can include skin temperature, pulse, respiratory rate, and physical activity/energy expended. Social data can include proximity, frequency of interaction, time of interaction, duration of interaction, geographical location, emotional/verbal contents, and tone and pitch in voice signals. For example, the social data can include a proximity of the subject to other persons wearing socio-biosensor devices and bio-behavioral data measured during the time the subject is in close proximity to other persons. Environmental data can include temperature, humidity, noise, and barometric pressure. The bio-behavioral data, social data, and/or environmental data can be used to assess the health impact of social interaction, as well as the quality of life of the subject. The subject can be, for example, an athlete, a veteran, an active duty military personnel, an elderly person, a person suffering from a disease or mental impairment, or a child.

The wearable socio-biosensor device 10 can include a body portion 12, an attachment mechanism 14, and a plurality of sensors 16a-n. Although three sensors 16a-n are illustrated, it will be understood that any number of sensors may be present, e.g., greater than or equal to two. The plurality of sensors 16a-n can be entirely or partially embodied within (e.g., enclosed or contained) and/or on the body portion 12 and/or the attachment mechanism 14. For example, at least one of the sensors 16a can be embodied within the attachment mechanism 14. The sensors 16a-n can include, for example, an electrode, an infrared emitter, an infrared detector, an accelerometer, a gyroscope, a thermistor, a thermometer, a microphone, a video recorder, a proximity sensor, a pulse sensor, a gas sensor, a barometer, and/or a humidity sensor. As another example, the sensors 16a-n can include a low power MEMS accelerometer, a skin temperature sensor, a pulse sensor, a proximity sensor (e.g., an RF emitter/detector), an ambient temperature sensor, or a humidity sensor.

In some instances, the wearable socio-biosensor device 10 can include a user interface (UI) 18 to display an indication of at least one of the bio-behavioral data, the social data, and/or the environmental data. For example, the UI 18 can provide feedback related to the recorded bio-behavioral data, social data, and/or environmental data. In some instances, the UI 18 can include an analog (audio or visual) indicator. For example, the UI 18 can include one or more LEDs that can be associated with one or more of the sensors 16a-n. The analog indicator can, for example, indicate when a given sensor 16a-n is active, when a given recording is made, a result of the given recording, a score determined from the recordings, the score exceeding a certain value, etc. In other instances, the UI 18 can include a GUI that can be used for comprehensive monitoring and analysis functionality.

In some instances, the wearable socio-biosensor device 10 can include a power (on/off) switch 20. The switch 20 can, for example, be used to conserve battery life. For example, the battery of the wearable socio-biosensor device 10 can record the bio-behavioral data, social data, and/or the environmental data for at least 12 hours without recharging. The battery life can be extended if the wearable socio-biosensor device 10 is switched off when not recording.

The wearable socio-biosensor device 10 can be configured to be worn by a subject without impeding natural activities. Additionally, the wearable socio-biosensor device 10 can be adaptable for use in indoor and/or outdoor environments. The wearable socio-biosensor device 10 can be worn by the subject for at least a portion of time when the subject is awake and/or asleep to facilitate the assessment of the health and quality of life of the subject.

The attachment mechanism 14 can be configured to attach and release the wearable socio-biosensor device 10 from the subject's body. For example, the attachment mechanism 14 can include Velcro, one or more magnets, a stretchable strap, or any other releasable mechanism.

The body portion 12, in some instances, can be configured with a small size, a lightweight material, and/or a modular design. The wearable socio-biosensor device 10 can be worn by the subject, for example, like a wrist watch, embedded in clothing, strapped across the chest under clothing, or in another non-obtrusive manner. The wearable socio-biosensor device 10 can be scalable so that subjects of different sizes can wear the wearable socio-biosensor device 10. In some instances, the wearable socio-biosensor device 10 can be constructed of low-cost materials.

Figure 2:
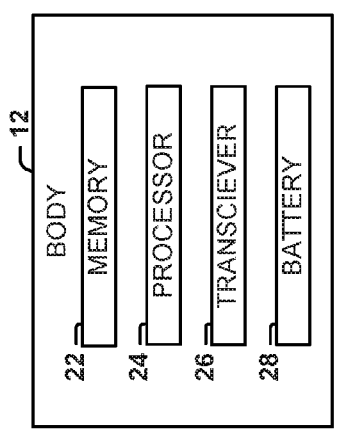
FIG. 2 is a block diagram showing an example of an interior of the body in FIG. 1.

An example of the interior of the body portion 12 is shown in FIG. 2. The body portion 12 can include a non-transitory memory 22, a processor 24, a wireless transceiver 26, and a rechargeable battery 28. In some instances, the body portion 12 can have additional elements, such as an input/output (I/O), one or more of the sensors 16a-n, or the like. In some instances, the body portion 12 can include modular elements so that different elements can be exchanged and replaced.

The non-transitory memory 22 can store instructions and data from the sensors 16a-n. For example, the data can include the bio-behavioral data, social data, and/or environmental data. The non-transitory memory 22 can be embodied at least in part in hardware and/or in software (including firmware, resident software, micro-code, etc.). Indeed, the non-transitory memory can be any non-transitory medium that is not a transitory signal and can contain or store data and instructions.

The instructions can be accessed by the processor 24, which can facilitate the execution of the instructions to perform actions, such as controlling when the sensors 16a-n acquire data, processing the data, calculating a score based on the data (e.g., a social interaction value), a value (e.g., likelihood of disease transmission, quality of life) based on the calculated score, or the like. For example, the processor 24 can be a processor of a general purpose computer, special purpose computer, and/or other programmable data processing apparatus to produce a mechanism for implementing the functions of the components (e.g., a series of operational steps of a computer-implemented process such that the instructions that execute on the computer or other programmable apparatus provide steps for implementing the functions of the components). As another example, the processor 24 can be a controller or a microcontroller. The rechargeable battery 28 can provide power to the processor 24.

The wireless transceiver 26 can include the functionality of a wireless transmitter and/or receiver. The wireless transceiver 26 can transmit and/or receive data to or from other wearable socio-biosensor devices 10 and/or a remote computing device. For example, when the remote computing device is a robot device, the wireless transceiver 26 can facilitate interaction between the wearable socio-biosensor device 10 and the robot device. For example, the robot device can be a social robot to engage and interact with the subject wearing the wearable socio-biosensor device. The wireless transceiver 26 can be powered by the rechargeable battery 28 and/or triggered to transmit data by the processor 24. The wireless transceiver 26 can be configured for short range data transmission and/or reception. For example, the wireless transceiver 26 can be configured for WiFi communication, Bluetooth communication, Xbee communication, or any other type of short range wireless communication. However, in some instances, the wireless transceiver 26 can be configured to long range data transmission and/or reception (e.g., cellular, global positioning satellite (GPS), etc.).

Figure 3:
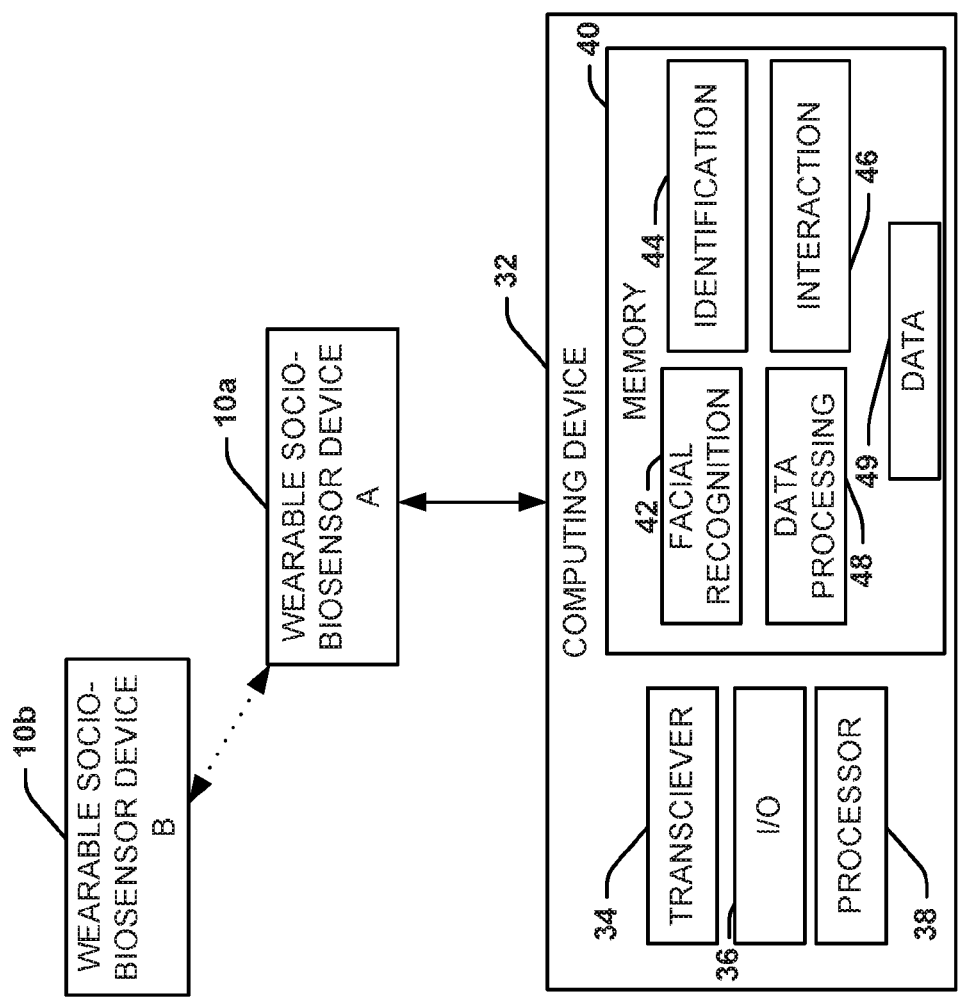
FIG. 3 is a block diagram showing an example of a system that can employ the wearable socio-biosensor device shown in FIG. 1.

Referring now to FIG. 3, illustrated is an example of a system within which the wearable socio-biosensor device 10 of FIG. 1 can be operational. Within the system, there can be one or more wearable socio-biosensor devices 10a, b. The one or more wearable socio-biosensor devices 10a, b can communicate with each other if they are within range of each other. One or more of the wearable socio-biosensor devices 10a, b can communicate with a remote computing device 32. In some instances, the remote computing device 32 can be a robot device that can interact with the subject (e.g., a social robot having an appealing look, such as a human, an animal or a cartoon robot). The remote computing device 32 can perform an analysis of the data collected by the wearable socio-biosensor devices 10a, b and provide alerts to the wearable socio-biosensor devices based on the analysis.

As an example, the remote computing device 32 can include components, including a transceiver 34 (e.g., a wireless transmitter and/or a wireless receiver), an I/O 36, a processor 38, and a non-transitory memory 40. Functions of one or more of the components can be implemented by computer program instructions that are stored in the non-transitory memory 40. These computer program instructions can be provided to the processor 38 for execution. The processor 38 can be a processor of a general purpose computer, special purpose computer, portable computing device, a smart phone, and/or other programmable data processing apparatus to produce a mechanism for implementing the functions of the components (e.g., a series of operational steps of a computer-implemented process such that the instructions that execute on the computer or other programmable apparatus provide steps for implementing the functions of the components).

The non-transitory memory 40 can be embodied at least in part in hardware and/or in software (including firmware, resident software, micro-code, etc.). Furthermore, aspects of the components stored in the non-transitory memory 40 can take the form of a computer program product on a computer-usable or computer-readable storage medium (the non-transitory memory 40) having computer-usable or computer-readable program code embodied in the medium for use by or in connection with an instruction execution system. A computer-usable or computer-readable medium can be any non-transitory medium that is not a transitory signal and can contain or store the program for use by or in connection with the instruction or execution of a system, apparatus, or device. The computer-usable or computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

The computer program instructions stored in the non-transitory memory can include a facial recognition algorithm 42, a subject identification algorithm 44, a subject interaction algorithm 46, and/or a data processing algorithm 48. The non-transitory memory 40 can also store data 49 related to the bio-behavioral data, social data, and environmental data received from the wearable socio-biosensor device 10a. In some instances, the data 49 can be processed by the data processing algorithm 48 to assess the health impact of social interaction and/or the quality of life of the subject (e.g., based on an assessed interpersonal relationship established between the subject and at least one other person wearing the other socio-biosensor device 10b). In other instances, at least a portion of the data 49 can be sent by the computing device 32 to another device at a central location (e.g., the CDC) for creation of a transmission map for an infectious disease.

As an example, the facial recognition algorithm 42 can be used to identify facial features of the subject. For example, the facial recognition algorithm 42 can include an image processing algorithm that can be based on an accelerated adaptive boosting classifier and/or a skin color filter. Based on the identified facial features, the subject identification algorithm 44 can be used to identify the subject. Once the subject is identified, the subject interaction algorithm 46, which can be personalized for the identified subject, can be executed. In some instances, the subject interaction algorithm 46 can provide personal assistance to the subject (e.g., monitoring a health of the subject, providing a medication alarm to the subject, providing encouragement to the subject to engage in social interaction with another person, and/or providing a weather report to the subject).

IV. Methods

Another aspect of the present disclosure can include a method 50 (FIG. 4) for establishing an interaction between a computing device and a wearer of a wearable socio-biosensor device (or "subject"). In some instances, the method 50 can be performed using the system shown in FIG. 3, which includes at least two wearers of wearable socio-biosensor devices 10a, b and a remote computing device 32. The method 60 (FIG. 5) is an example of the operation of the wearable socio-biosensor device. In some instances, the method 60 can be performed using the wearable socio-biosensor device 10 shown in FIG. 1. The method 70 (FIG. 6) can provide for personalized interaction between a computing device and a wearer of the wearable socio-biosensor device 10. In some instances, the method 70 can be performed using the system shown in FIG. 3, which includes at least two wearers of wearable socio-biosensor devices 10a, b and a computing device 32.

Figure 4:
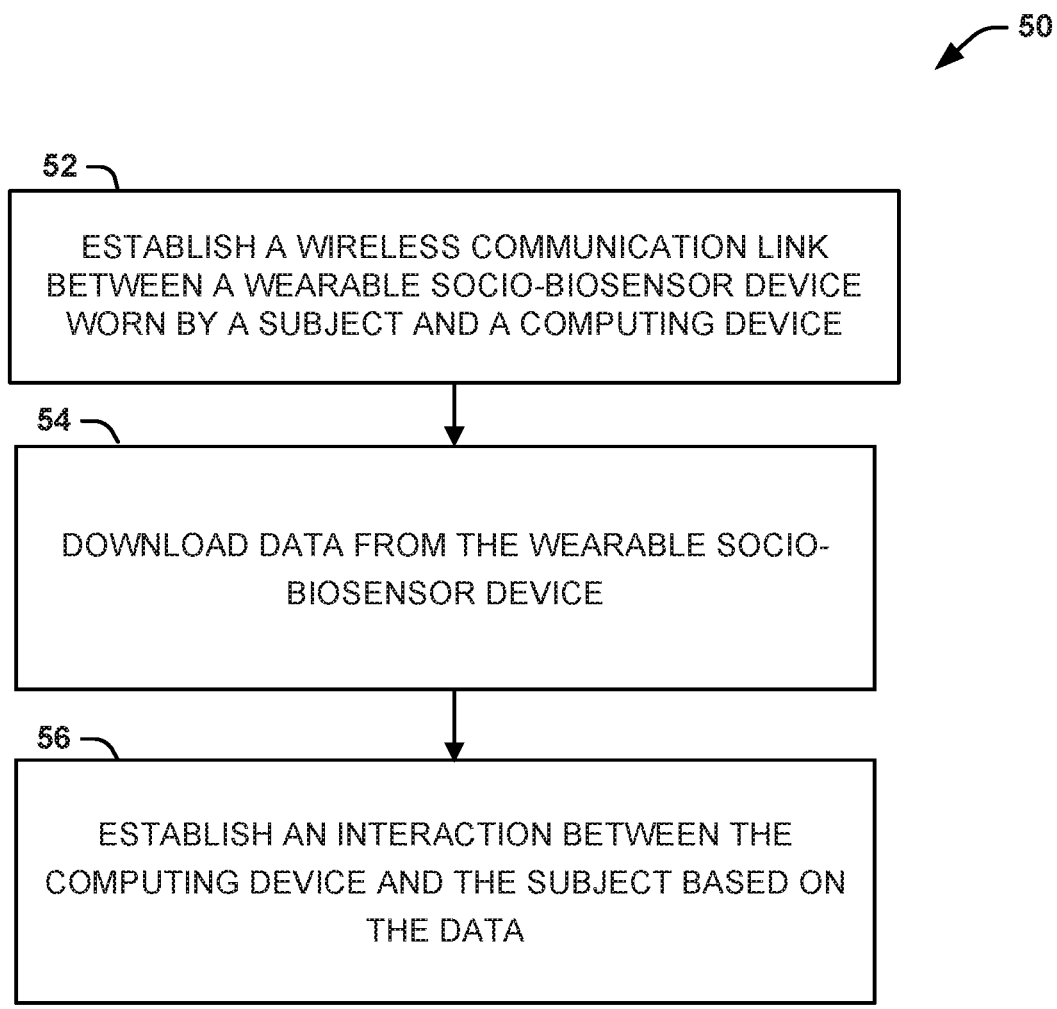
FIG. 4 is a process flow diagram illustrating a method for establishing an interaction between a computing device and a wearer of a socio-biosensor device according to another aspect of the present disclosure.
Figure 5:
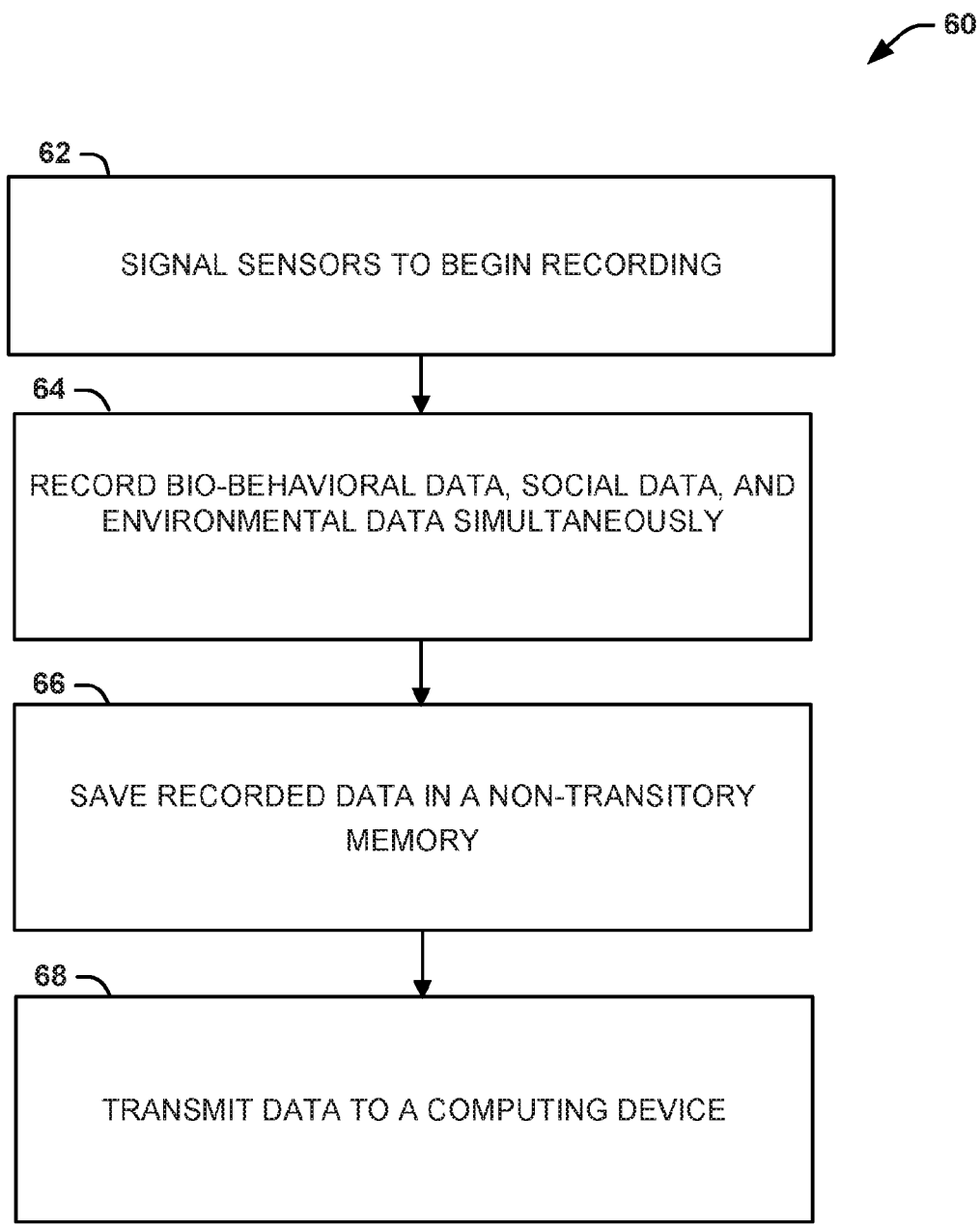
FIG. 5 is a process flow diagram illustrating a method for operating the a wearable socio-biosensor device according to another aspect of the present disclosure.
Figure 6:
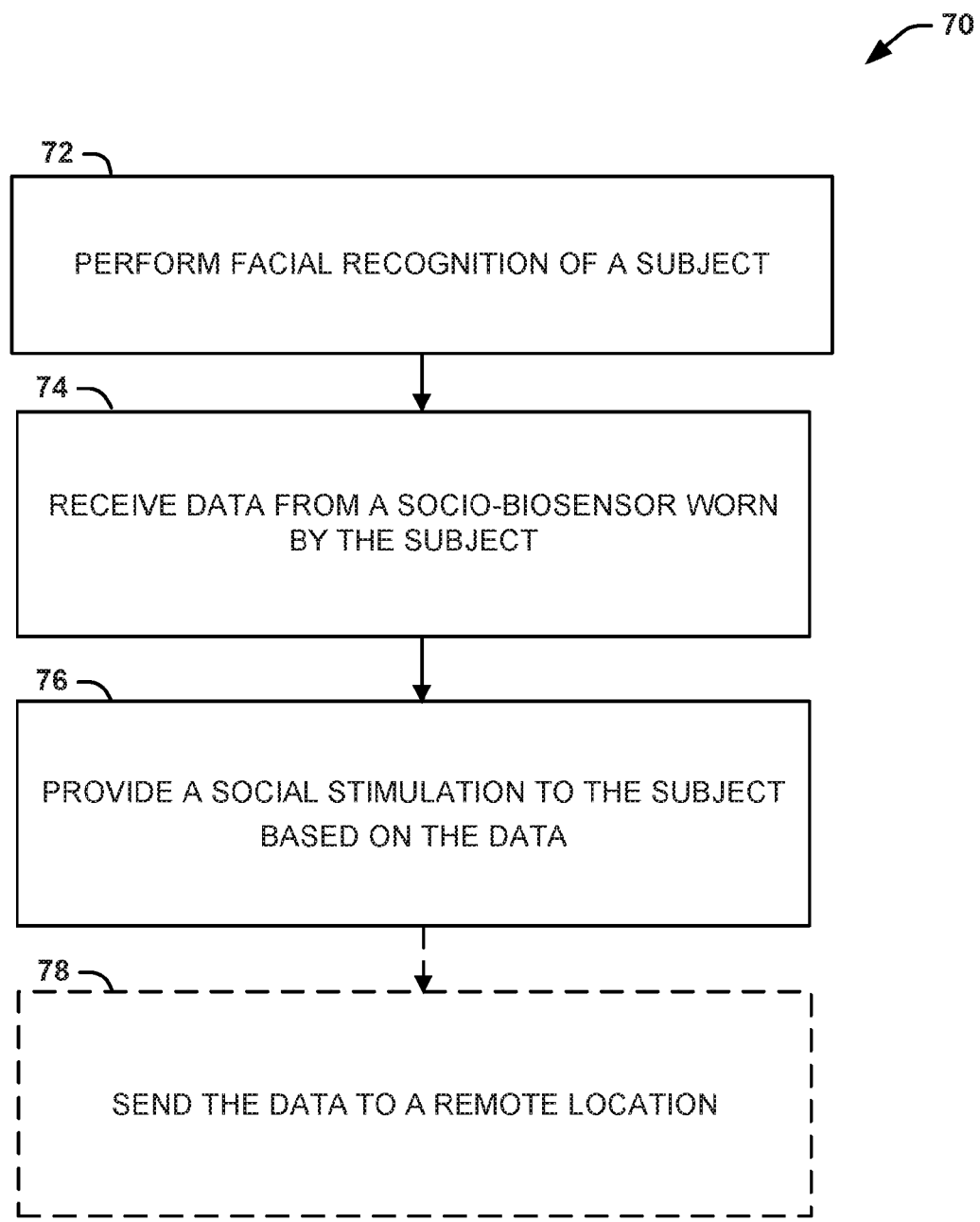
FIG. 6 is a process flow diagram illustrating a method for personalized interaction with a subject wearing a socio-biosensor device according to another aspect of the present disclosure.

The methods 50-70 of FIGS. 4-6, respectively, are illustrated as process flow diagrams with flowchart illustrations. For purposes of simplicity, the methods 50-70 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50-70.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 50-70 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Referring now to FIG. 4, illustrated is a method 50 for establishing an interaction between a computing device (e.g., computing device 32, such as a social robot with a non-threatening human-like, cartoon-like, or animal-like appearance) and a wearer of a socio-biosensor device (e.g., wearable socio-biosensor device 10). At 52, a wireless communication link can be established between a wearable socio-biosensor device 10 worn by a subject and a computing device 32. For example, the wireless communication link can be a short-range communication link according to a WiFi protocol, a Bluetooth protocol, a Xbee protocol, or the like. At 54, data can be downloaded from the wearable socio-biosensor device 10 to the computing device 32. The data can include bio-behavioral data of the subject, social data related to a proximity of the subject to other persons, and/or environmental data related to the subject's environment. At 56, an interaction can be established between the computing device 32 and the subject based on the data. The interaction can be, for example, providing a social stimulation from the computing device 32 to the subject. As another example, the social stimulation can be providing personal assistance by the computing device 32 to the subject (e.g., monitoring a health of the subject, providing a medication alarm to the subject, providing encouragement to the subject to engage in social interaction with another person, and/or providing a weather report to the subject).

Illustrated in FIG. 5 is a method 60 for operating the wearable socio-biosensor device (e.g., wearable socio-biosensor device 10). At 62, signals within the wearable socio-biosensor device are signaled to begin recording. At 64, bio-behavioral data, social data, and/or environmental data are recorded simultaneously. At 66, the recorded data is saved in a non-transitory memory of the socio-biosensor device. At 68, the data can be transmitted to a remote computing device (e.g., computing device 32).

Referring now to FIG. 6, illustrated is a method 70 for personalized interaction (by computing device 32, such as a social robot with a human, cartoon, or animatronics appearance) with a subject wearing a wearable socio-biosensor device. At 72, a facial recognition procedure can be performed to identify the subject. For example, the facial recognition procedure can be based on based on an accelerated adaptive boosting classifier and a skin color filter. At 74, data can be received from a wearable socio-biosensor device worn by the subject. At 76, a social stimulation can be provided to the subject based on the data. In some instances, the data can be sent to a remote location for further processing (e.g., to create a transmission map of a disease based on social interaction).

V. Examples

The following examples illustrate several applications of the socio-biosensor device described above.

Example Hardware Prototype

A hardware prototype of the wearable socio-biosensor can provide for simultaneous measurement of bio-behavioral, social, and environmental data. A low-cost and low-power MEMS accelerometer, skin temperature sensor, and pulse sensor were integrated for physical activity recognition and health monitoring. A method using the RF-based signal strength was adopted to measure the proximity among users to determine the frequency and time duration of social interaction. Environmental monitoring focused on the ambient temperature and humidity. Collected data is saved on a microSD card and can be sent to the host computer for real-time monitoring and further data analysis. The data analysis was performed using MATLAB to determine the thresholds of user proximity for relative localization. Sensor data was evaluated in different experimental scenarios.

In one design, the body included two boxes for more freedom of motion with a low overall size. Each box measured 1.85"×1.85'×0.875'. Velcro bands were used as the attachment mechanism to secure the body to the subject's wrist. The pulse sensing module was held in place using the Velcro band. The battery was a rechargeable battery. Wireless communication was accomplished via a Xbee module for communication between multiple devices and a computer hub.

In another design, the body included a single box with a translucent cover so that LED status lights can be seen by the subject. A cover was made from a 3-D printed flexible filament; the main box was 3-D printed ABS. Rubber was incorporated for the bottom and the side of the device to increase the comfort for the subject. An adjustable rubber strap that can be fastened using magnets was used as the attachment mechanism. The pulse sensor can be moved along the rubber strap to be placed in the optimal location by the user. An Arduino Pro-Mini microcontroller was used as the processor. A power switch was accessible from the side using a pen or finger. The battery was a rechargeable battery. Wireless communication was accomplished via a Xbee module for communication between multiple devices and a computer hub.

Infectious Disease Screening

A wearable, wireless socio-biosensor system can facilitate early screening of infectious diseases in developing countries. This wearable wireless socio-biosensor collects multi-dimensional diagnostic data (e.g., bio-behavioral data, social data, and environmental data) simultaneously from those who are at high risk of acquiring human-to-human transferable infectious diseases (e.g., Tuberculosis (TB), human immunodeficiency virus (HIV), and Ebola) in a non-invasive and non-intrusive manner. The bio-behavioral data includes skin temperature, pulse, and physical activity. The environmental data includes ambient temperature and humidity. The social data includes location, distance, frequency, and duration of social interactions among the sensor users.

Transmission of the infectious diseases can be tracked based on the data collected. The wearable socio-biosensor device provides the capability of objective measurements of intensity, times, and locations of social interaction and synchronized social, biological, and environmental data collection among multiple users. Accordingly, this enables early detection of symptoms, reduces the number of physical contacts between the infected and the non-infected, and provides data and the intensities, times, and locations of social interaction in addition to the individual's bio-behavioral and environmental data. The wearable socio-biosensor device can provide wireless monitoring of bio-behavioral, environmental, and social data for a group of people at high risk of acquiring an infectious disease in developing countries. This technology can be supplemental or alternative to the current contact follow-up procedure for infectious diseases. The socio-biosensor technology can be available at a relatively low cost (<$100 each) and can provide early screening of the various infectious diseases that often come with significant individual and societal costs.

The socio-biosensor is equipped with a pulse sensor, thermister for skin temperature, thermometer for ambient temperature, humidity sensor, triaxial accelerometer for physical activity, and short- and long-distance wireless communication modules (i.e., GPS and XBee/Bluetooth). While skin temperature measured in wrist can be lower and more variable than core body temperatures, existing evidence suggest a strong correlation between the two.

An embedded user feedback mechanism can be used for indicating abnormal pulse rate or fever. The sensor is water-resistant and easily disinfected by commercial grade disinfectants. GPS is used to track the user's geographical locations (usually for outdoors) with a resolution of about 2 meters. A radio-based short-distance wireless communication module measures relative positions and distance among the users in less than about 2 meters with the resolution of about an inch. Two options for daily data collection were considered and examined: using existing cellular network and the users' cellular phone or using a host computer with existing internet connection.

Older Veterans in Assisted Living Facility—Quality of Life

The socio-biosensor can facilitate the assessment of biological, behavioral, social, and physical environmental data and the examination of their interactive roles and relative importance to older veterans. The socio-biosensor enables low-cost health monitoring that can foster the older veterans independent living. The social interaction data can lead researchers and clinicians to better understanding of its health impact and further to design social intervention programs to enhance the veterans' quality of life.

The socio-biosensor measures air pollutants, temperature, and humidity as environmental factors; skin temperature, heart rate and respiratory rate as biological variables and also stress indicators; physical activity as a behavioral factor; and interpersonal relationships among the users as a social factor. Social data was measured by the sensors by the physical proximity and verbal communication data analyzed as follows. Physical proximity will be determined by the differences in the wireless signal strength and localization techniques. Outcome measures include the total duration, frequency, and average time that each individual interacts with others in the setting. A composite proximity score (Pscore) is calculated by the averaged total time that any two or more people are within 2 meters of distance and scored into a 1 to 10 scale.

Verbal communication analysis was based on three levels of observation, encompassing three aspects of communication: conversation, prosody, and voice. By conversational analysis, 17 recorded speech data will be categorized by different psychological attitudes (e.g., suspicion, doubt, indecision), emotions (e.g., anger, fear, surprise) and intentions, as well as linguistic information, like sentence types (e.g., declarations, interrogatives, imperatives), focus, semantic and syntactic contents. The outcome was calibrated into a composite verbal interaction score (Vscore) with a scale of 1 to 10, where 1 being the most negative and 10 being the most positive based on the quantity of each positive/neutral/negative verbal categories. Words and discussions are only analyzed for the psychological attitudes, emotions and intentions. The participants were free to turn the sensor off if there are conversations occurring that they do not wish recorded.

Health Assessment of Veterans and Active Duty Personnel

A modular, wearable socio-biosensor system was developed for simultaneous assessment of bio-behavioral, social, and environmental data and examination of their interactive roles in health and quality of life for veterans and active duty military personnel. The socio-biosensor provides an approach to autonomously measure quantitative social interaction data measured by physical distance, geographical location, and frequency and time duration of interaction and qualitative social interaction data measured by emotional status and stress level. This leads to improve health with increased self-awareness by continuous monitoring of an individual's health data and environmental exposures to provide user feedback. The technology provides for the wireless, simultaneous, and real-time measurement of bio-behavioral, social, and environmental data in any environmental condition. Additionally, the capability of measuring social data and conducting a social data assessment creates novelty in that social interaction has significant impact on human health by directly or indirectly improving physical and psychological well-being, the patterns and characteristics of social interaction can be directly related to human-to-human transmission of several infectious diseases, such as Influenza, HIV, Ebola, and Tuberculosis, and wireless communication among the sensors can be used for soldiers to detect and locate wounded peer soldiers even when no communication with the base is available.

The wearable socio-biosensor has a "modular" architecture for the hardware. The sensor consists of a core module (M0) and two additional modules (M1 & M2). M0 contains sensors and a main processor for measuring bio-behavioral and sensor-to-sensor proximity data. M1 contains a GPS and sensors for measuring environmental data, and M2 includes a voice recording and processing system for qualitative social data. The modular design allows customization of the sensors depending on target measures and environmental setting.

Socially Assistive Robot

An integrative technology, CoRobot, can be used with the wearable socio-biosensor device and personalized for interaction with a recognized subject (e.g., based on facial recognition algorithms). The CoRobot system can improve the quality of life by augmenting social interactions through social stimuli provided by the robot (e.g., stylized to be non-threatening, such as animal shaped or cartoon robot shaped) and enabling autonomous and real time assessment of individual bio-behavioral, environmental, and social data. The socially assistive robot can interact with older people via vision/sound/touch-based interaction and wearable telesensors that can measure the user's biological, behavioral, environmental, and social data. The CoRobot brings positive impact for older people, in particular for those living alone in their own homes and living in assisted living facilities, by providing strong evidence of the potential utility of social robots for improving the quality of life. CoRobot can also be used in hospitals and long-term care facilities. The potential impact of this research reaches beyond older people. CoRobot can be further used for behavioral and social training, cognitive rehabilitation, and further physical trainings and assessment. The CoRobot technology can also be used in other technologies, such as a robotic wheelchair, a robot to perform household tasks, a robot lift for a subject, and the like.

From the above description, those skilled in the art will perceive improvements, changes and modifications. Such improvements, changes and modifications are within the skill of one in the art and are intended to be covered by the appended claims.

What is claimed is:

1. A wearable socio-biosensor device comprising:
a plurality of sensors to detect bio-behavioral data of a subject, social data related to a proximity of the subject to other persons wearing socio-biosensor devices and bio-behavioral data measured during the time the subject is in close proximity to other persons, and environmental data related to the subject's environment;
a body portion comprising:

a non-transitory memory to store the bio-behavioral data, the social data, and the environmental data;
a processor;
a wireless transceiver to communicate with another device based on at least one of the bio-behavioral data, the social data, and the environmental data; and
a rechargeable battery; and
an attachment mechanism that facilitates attachment of the body portion to the subject,
wherein at least one of the plurality of sensors is embodied in the attachment mechanism.

2. The wearable socio-biosensor device of claim 1, further comprising a user interface to display an indication of at least one of the bio-behavioral data, the social data, or the environmental data.

3. The wearable socio-biosensor device of claim 1, wherein the processor determines a social interaction value based on the bio-behavioral data, the social data, and the environmental data.

4. The wearable socio-biosensor device of claim 3, wherein the processor determines a likelihood of infectious disease transmission to or from the subject based on the social interaction value,
wherein the infectious disease is at least one of ebola, tuberculosis, and human immunodeficiency virus (HIV).

5. The wearable socio-biosensor device of claim 1, wherein the processor determines a quality of life of the subject based on the social interaction value,
wherein the social interaction value indicates a level of a personal relationship of the subject and at least one other person with another socio-biosensor device and is based on at least one of a physical proximity to the at least one other person, a frequency of vocal interaction the at least one other person, an emotional status of the subject, a stress level of the subject, and geographical locations of the subject and the at least one other person.

6. The wearable socio-biosensor device of claim 1, wherein the processor triggers the plurality of sensors to begin the detection upon determining that the subject is engaged in an activity or a social interaction.

7. The wearable socio-biosensor device of claim 1, wherein the plurality of sensors comprise at least two of an electrode, an infrared emitter, an infrared detector, an accelerometer, a gyroscope, a thermistor, a thermometer, a microphone, a video recorder, a proximity sensor, a pulse sensor, a gas sensor, a barometer, and a humidity sensor.

8. The wearable socio-biosensor device of claim 1, wherein the bio-behavioral data comprises at least one of skin temperature, a pulse, a respiratory rate, and an energy expended by the subject.

9. The wearable socio-biosensor device of claim 1, wherein the wireless transceiver communicates with a robot device to facilitate interaction with the robot device.

10. A method comprising:
establishing a wireless communication link between a wearable socio-biosensor device worn by a subject and another device;
downloading data from the wearable socio-biosensor device to the another device over the wireless communication link, wherein the data comprises bio-behavioral data of the subject, social data related to a proximity of the subject to other persons, and environmental data related to the subject's environment; and
establishing an interaction between the another device and the subject based on the downloaded data.

11. The method of claim 10, wherein the wearable socio-biosensor device comprises:
a plurality of sensors to detect the bio-behavioral data, the social data, and the environmental data;
a body portion comprising:
a non-transitory memory to store the bio-behavioral data, the social data, and the environmental data;
a processor;
a wireless transceiver to communicate with the another device; and
a rechargeable battery; and
an attachment mechanism that facilitates attachment of the body portion to the subject,
wherein at least one of the plurality of sensors is embodied in the attachment mechanism.

12. The method of claim 10, wherein the another device comprises a robot, wherein the robot comprises:
a wireless communication module to interface with the socio-biosensor device to receive the data; and
a processor to recognize a person associated with the socio-biosensor device and to process the data to facilitate the interaction.

13. The method of claim 12, wherein the robot comprises a human-like or an animal-like appearance.

14. The method of claim 10, wherein the interaction comprises providing a social stimulation from the another device to the subject.

15. The method of claim 14, wherein the social stimulation comprises providing personal assistance to the subject,
wherein the personal assistance comprises at least one of monitoring a health of the subject, providing a medication alarm to the subject, providing encouragement to the subject to engage in social interaction with another person, and providing a weather report to the subject.

16. The method of claim 10, further comprising recognizing a face of the subject by the another device using an image-processing algorithm,
wherein the image-processing algorithm comprises at least one of an accelerated adaptive boosting classifier and a skin color filter.

17. A system comprising:
a wearable socio-biosensor device, comprising:
a plurality of sensors to detect bio-behavioral data of a subject, social data related to a proximity of the subject to other persons, and environmental data related to the subject's environment;
a body portion comprising:
a non-transitory memory to store the bio-behavioral data, the social data, and the environmental data;
a processor;
a wireless transceiver to communicate with another device based on at least one of the bio-behavioral data, the social data, and the environmental data; and
a rechargeable battery; and
an attachment mechanism that facilitates attachment of the body portion to the subject,
wherein at least one of the plurality of sensors is embodied in the attachment mechanism; and
another device, comprising:
a wireless communication module to interface with the socio-biosensor device to receive the bio-behavioral data, the environmental data, and the social data; and
a processor to recognize the subject, process the bio-behavioral data, the social data, and the environmental data, and facilitate an interaction between the another device and the subject.

18. The system of claim 17, wherein the another device comprises a social robot.

19. The system of claim 17, wherein the another device sends the processed bio-behavioral data, social data, and environmental data to a central location to create a transmission map of an infectious disease.

20. The system of claim 17, wherein the another device determines a quality of life of the subject based on an assessed interpersonal relationship between the subject and at least one other person wearing another socio-biosensor device.

* * * * *